United States Patent
Linnarsson

(10) Patent No.: US 7,168,852 B2
(45) Date of Patent: Jan. 30, 2007

(54) METHOD AND A DEVICE FOR THERMAL ANALYSIS OF CAST IRON

(75) Inventor: Henrik Linnarsson, Katrineholm (SE)

(73) Assignee: SinterCast AB, Stockholm (SE)

( * ) Notice: Subject to any disclaimer, the term of this patent is extended or adjusted under 35 U.S.C. 154(b) by 56 days.

(21) Appl. No.: 10/498,121

(22) PCT Filed: Dec. 17, 2002

(86) PCT No.: PCT/SE02/02353

§ 371 (c)(1),
(2), (4) Date: Jun. 9, 2004

(87) PCT Pub. No.: WO03/064714

PCT Pub. Date: Aug. 1, 2003

(65) Prior Publication Data

US 2005/0031015 A1    Feb. 10, 2005

(30) Foreign Application Priority Data

Dec. 17, 2001   (SE)   ..................... 0104252

(51) Int. Cl.
*G01K 1/00*   (2006.01)
*G01K 7/00*   (2006.01)

(52) U.S. Cl. .............. 374/139; 374/179; 374/208
(58) Field of Classification Search .............. 374/139, 374/13, 157, 113
See application file for complete search history.

(56) References Cited

U.S. PATENT DOCUMENTS 3,882,727 A * 5/1975 Clark et al. ................. 374/208
4,474,640 A * 10/1984 Wan ............................. 117/55
4,598,754 A * 7/1986 Yen et al. ..................... 164/4.1
4,778,281 A * 10/1988 Falk .............................. 374/140
5,577,841 A * 11/1996 Wall ............................. 374/140
5,720,553 A * 2/1998 Falk .............................. 374/26
5,863,123 A * 1/1999 Lee .............................. 374/179
5,869,343 A    2/1999 Handschuck et al.
6,102,981 A * 8/2000 Lindholm ..................... 75/382
6,604,016 B1* 8/2003 Andersson ................... 700/204
2005/0069018 A1* 3/2005 Hosler et al. .................. 374/139

FOREIGN PATENT DOCUMENTS

| DE | 39 00 943 C1 |   | 1/1990 |
| JP | 07092158 A | * | 4/1995 |
| SE | 626450 A | * | 11/1981 |
| SU | 438910 A | * | 1/1975 |
| WO | 86/01755 A1 |   | 3/1986 |
| WO | 92/06809 |   | 4/1992 |
| WO | 96/23206 A1 |   | 8/1996 |
| WO | 99/25888 |   | 5/1999 |
| WO | 99/28726 A1 |   | 6/1999 |

* cited by examiner

Primary Examiner—Diego Gutierrez
Assistant Examiner—Mirellys Jagan
(74) Attorney, Agent, or Firm—Nixon & Vanderhye P.C.

(57) ABSTRACT

The present invention provides a novel method and a system of modules for carrying out thermal analysis of cast iron melts. The characterizing step of the method is de-termination of the position of the thermocouples used for recording cooling curves. The system comprises a thermocouple unit, a thermocouple holder, and a sampling unit. The system comprises means for ensuring that the thermocouples are correctly positioned before starting the thermal analysis. The system also comprises means for automatically transferring calibration data regarding the thermocouples.

6 Claims, 3 Drawing Sheets

METHOD AND A DEVICE FOR THERMAL ANALYSIS OF CAST IRON

Figure 1:
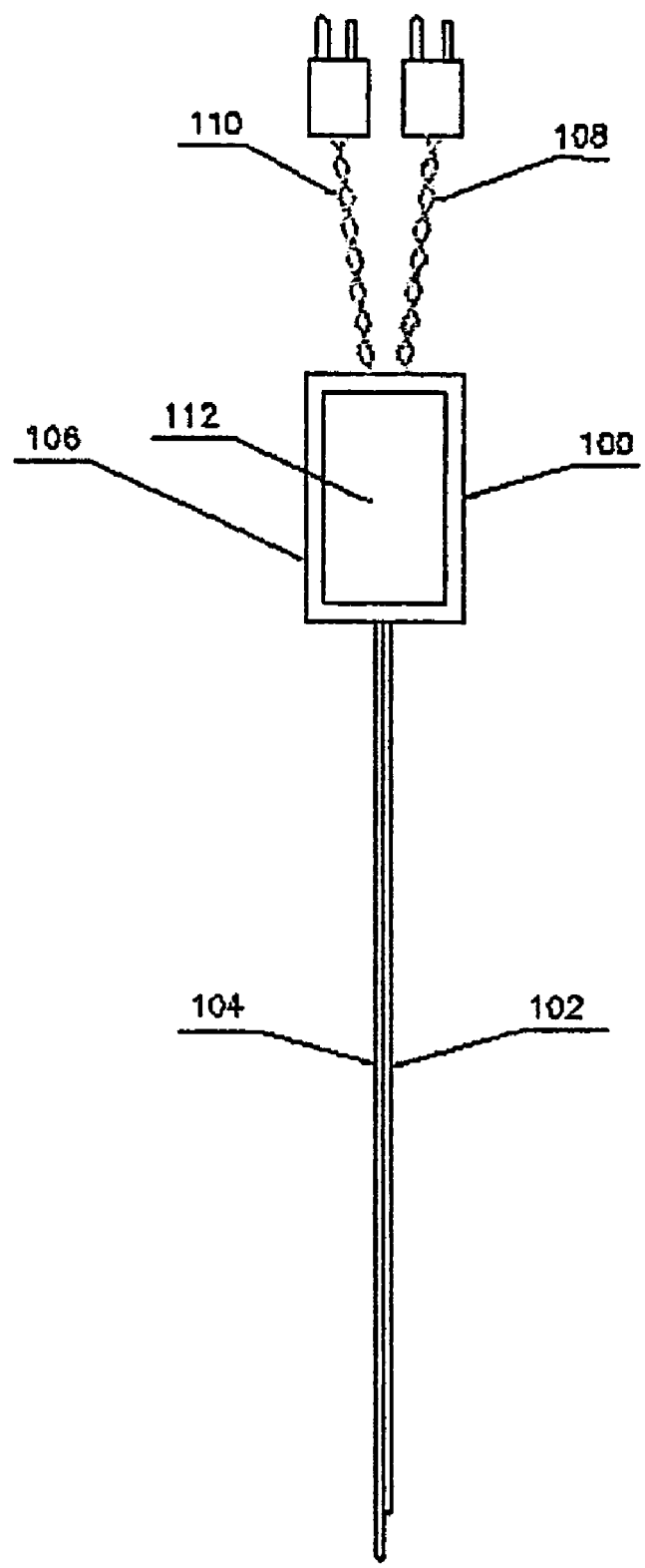

This application is a US national phase of international application PCT/SE02/02353 filed in English on 17 Dec. 2002, which designated the United States. PCT/SE02/02353 claims priority to SE Application No. 0104252-2 filed 17 Dec. 2001. The entire contents of these applications are incorporated herein by reference.

The present invention relates to an improved apparatus for carrying out thermal analysis of molten metals, in particular cast iron melts. The invention also relates to thermal analysis methods involving use of the improved apparatus.

TECHNICAL BACKGROUND

Thermal analysis, is a technique for determining and predicting the microstructure in which a certain molten substance, such as a molten metal or a molten alloy, will solidify. Such a thermal analysis is basically carried out by recording a so-called cooling curve showing the temperature variations as the molten sample transitions from the liquid state to the solid state, and then comparing the curve with pre-recorded calibration data. Cooling curves have been extensively used in the experimental study and production control of cast irons.

Thermal analysis is typically carried out by taking a sample of the melt to be analysed, and bringing the sample into a sample vessel. Then, cooling curves are recorded in the sample during solidification by means of temperature-responsive means, such as thermocouples or pyrometers.

Methods for predicting the microstructure with which a certain cast iron melt will solidify are known in the art. WO 99/25888 and WO 92/06809 disclose two examples of such methods. When carrying out the methods of both WO 99/25888 and WO 92/06809, a sample of molten cast iron is taken and subsequently the sample is transferred to a sample vessel. When the sample solidifies in the vessel, two cooling curves are recoded. One of the curves is recorded in the centre of the sample, whereas the other is recorded close to the sample vessel wall. Examples of suitable sample vessels that can be used in these methods are disclosed in WO 96/23206 and WO 99/28726.

When carrying out such prediction methods, it is essential that the underlying temperature measurements are obtained under constant conditions. A substantial amount of calibration has to be carried out. The sample amounts must be substantially identical. The sample vessels in which the cooling curves are recorded must also be substantially identical. Small differences regarding the sample vessels, sample amounts, thermocouple locations, etc. can lead to prediction errors. The industrial tolerance level regarding castings having an erroneous microstructure is very low, due to the substantial costs involved in quality control and potentially recalling of sold products. It is therefore essential to be able to carry out such thermal analysis methods for predicting the microstructure in which a certain cast iron melt will solidify under as constant conditions as possible.

SUMMARY OF THE INVENTION

The present invention provides a novel method and a system of modules for carrying out thermal analysis of cast iron melts. The characterizing step of the method is determination of the position of the thermocouples used for recording cooling curves. The system comprises a thermocouple unit, a thermocouple holder, and a sampling unit. The system comprises means for ensuring that the thermocouples are correctly positioned before starting the thermal analysis. The system also comprises means for automatically transferring calibration data regarding the thermocouples.

DETAILED DESCRIPTION OF THE INVENTION

As already mentioned, the present invention provides a method as well as a sampling module kit which is useful in thermal analysis of molten cast irons. By using the method and the kit as well as at least one of its components, it is possible to substantially increase the accuracy of such a thermal analysis, and to eliminate some sources of measurement variation and thus prediction error. Accordingly, the method, the kit and the components of the invention should be attractive to use in industrial processes for manufacturing cast iron products, where the tolerance level regarding erroneous castings is very low.

As disclosed herein, the term "cooling curve" refers to graphs representing the temperature as a function of time, which graphs have been recorded in the manner disclosed in WO 99/25888 and WO 92/06809.

The term "sample vessel" as disclosed herein refers to a small sample container which, when used for thermal analysis, is filled with a sample of molten metal. The temperature of the molten metal is then recorded in a suitable way. The walls of the sample vessel may be coated with a material which reduces the amount of structure-modifying agent in the melt in the immediate vicinity of the wall. Examples of such sample vessels are given in WO 99/28726 and WO 96/23206

The term "structure-modifying agent" as disclosed herein, relates to compounds either promoting spheroidization or precipitation of the graphite present in the cast iron. Suitable compounds can be chosen from the group of inoculating substances well-known in the art, and shape-modifying agents, such as magnesium, cerium and other rare earth metals. The relationship between the concentration of structure-modifying agents in molten cast irons and the graphite morphology of solidified cast irons have already been discussed in WO 92/06809 and WO 86/01755.

Figure 2:
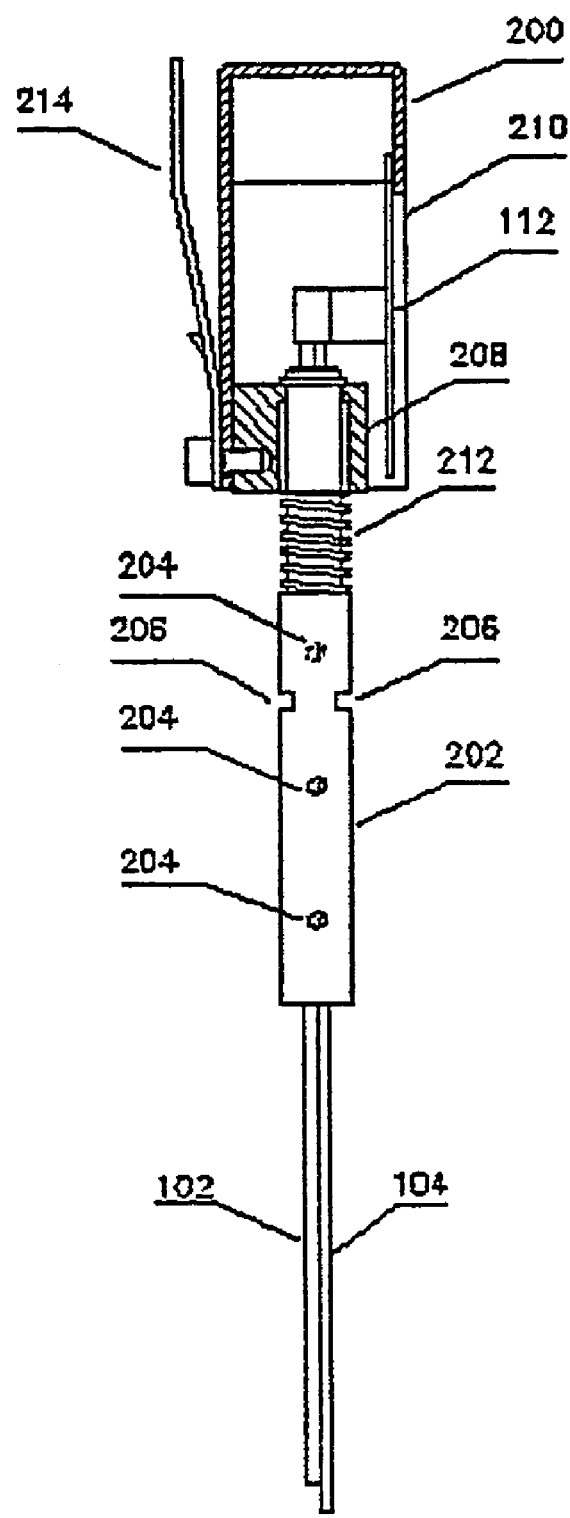
Figure 3:
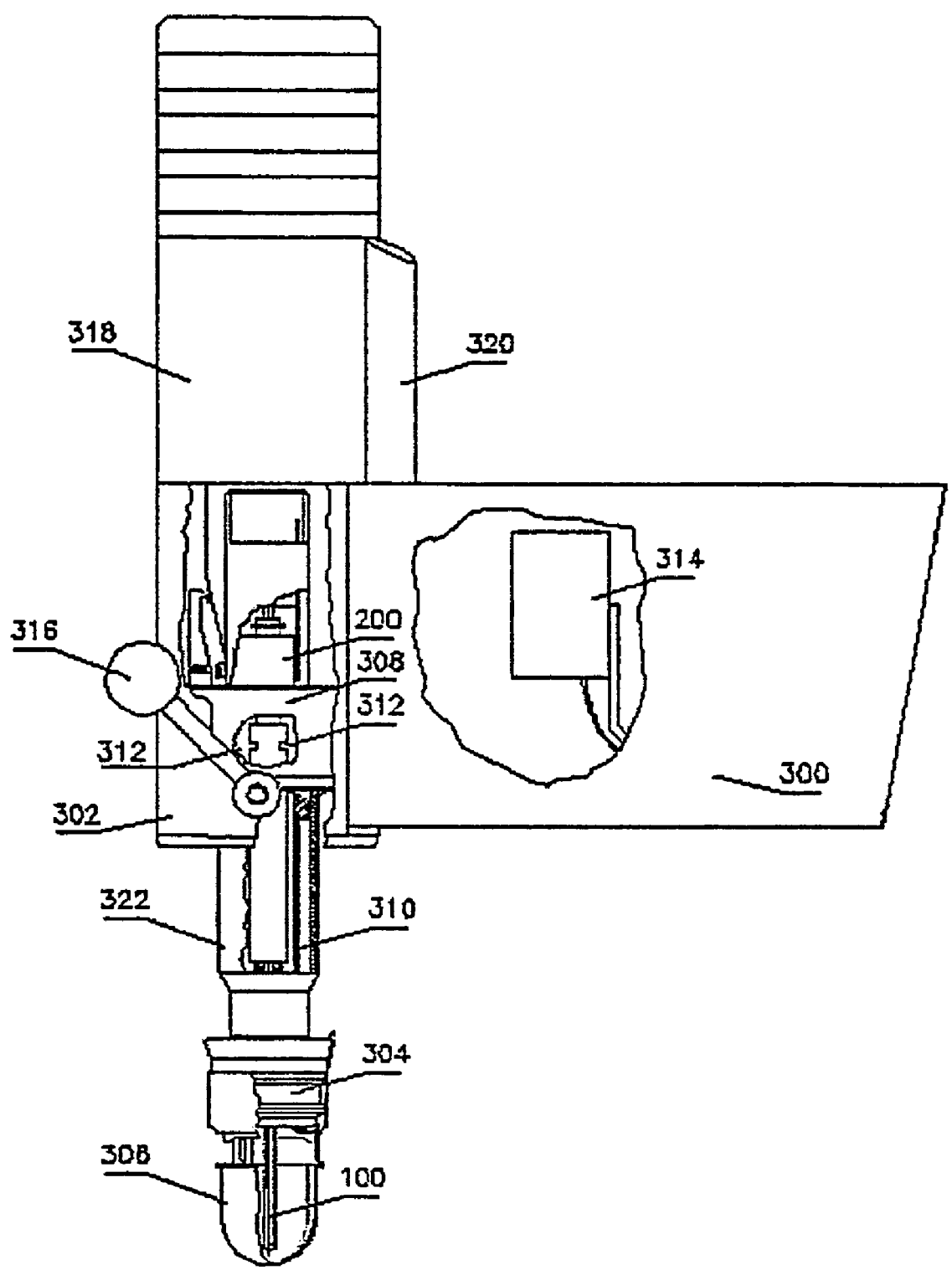

The present invention will be described with reference to the enclosed figures, in which:

FIG. 1 shows a thermocouple unit;

FIG. 2 discloses a thermocouple holder, which is adapted for containing a thermocouple unit. Details of the thermocouple unit are shown with broken lines;

FIG. 3 shows a sampling unit adapted to be used together with, and to contain, a thermocouple holder and a thermocouple unit. Details of a thermocouple holder and a thermocouple unit are shown with broken lines.

In a first aspect, the present invention relates to a method for predicting the microstructure in which a certain cast iron melt will solidify. The method is based on a known procedure, where a sample of a certain cast iron melt is obtained in a sample vessel. Then, cooling curves are recorded in the centre of the sample and in the vicinity of the sample vessel wall using two thermocouples. Finally, the cooling curves are evaluated using pre-recorded calibration data in order to predict the microstructure.

Thermal analysis methods involving recording cooling curves require pre-determined and constant conditions. An essential feature of such methods is use of pre-determined calibration data. The results of determinations made under slightly different conditions compared to the conditions during the calibration cannot be trusted. A common reason for erroneous results is that at least one of the thermocouples has been in a different position compared to the position during the calibration measurements. The present method therefore comprises a step where the positions of the thermocouples are determined before recording the cooling curves. If the position of one of the thermocouples differs from the calibration position with more than a predetermined value, a fault signal is activated and the sampling procedure cannot be initiated until the fault has been rectified.

The thermal analysis methods of WO 99/25888 and WO 92/06809 are all carried out within the temperature range 1100–1300° C. and with a tolerance of +/−1° C. When measuring temperatures within the above disclosed range and precision, the exact location of the temperature-responsive means is extremely important. An erroneous localisation of the temperature-responsive means of 1 mm in a typical sample vessel such as those vessels disclosed in WO 99/28726 and WO 96/23206, corresponds to an erroneous temperature measurement of 1.5° C.

The most important temperature measurements are all carried out within a subrange or "window" of +/−20° C. Small differences (~1.5° C.) regarding temperature measurements within this window may lead to very different predictions regarding the microstructure of the produced casting. Moreover, as the desired subrange or window comprises as much as +/−20° C. it is not possible for computer-based systems to detect erroneously located temperature responsive means by just monitoring the measured temperature.

An erroneous reading can therefore effect the production of castings with production stop, or worse, faulty products, because the process control system receives faulty data. In case any products are produced out of specification without any indication by the process control system, it may lead to quality problems.

It is therefore very important to be able to detect the exact location of the temperature-responsive means.

There are several reasons why a temperature-responsive means could be erroneously located. There could be small particles in its way. Alternatively, the temperature-responsive means could be bent and thus not be able to slide into the protective tube of the sample vessels normally used in these thermal analysis methods. There is no visual way to detect whether said means is in the correct position after mounting the sample vessel. Finally, the sample vessel could have been damaged during transport or mounted in a wrong manner, which also results in an erroneous location. There are several ways of determining the position of the thermocouples. The positions can for example be determined mechanically, optically or magetically. In the methods of WO 99/25888 and WO 92/06809, the thermocouples are moved from a resting position above the sample vessel to a measuring position in the cast iron melt. If position indication means are fixed to the thermocouples, or alternatively, to a protective tube completely surrounding the thermocouples it is possible determine the exact location of the thermocouple in the sample in relation the calibration position.

As disclosed herein, the term "position indication means" is intended to mean anything detectable that can be joined to a specific part of the thermocouple. The position of the thermocouple can be mechanically detected if the position indication means physically contacts a detection sensor. The location can be optically detected if the position indication means affect a radiation beam between a radiation source and a radiation detector. Likewise, the position can be magnetically detected if the position indication means affects or induces a magnetic field in the vicinity of the thermocouple. The position of the position indication means is preferably detected in a non-mechanical way, i.e. optical detection and magnetic detection are preferred. In case mechanic detection is used, there is a risk that wearing out of the detection equipment might hamper the results.

In a second aspect, the present invention relates to a sampling module kit suitable for carrying out the method of the first aspect. This sampling module kit comprises three parts operating together, namely a thermocouple unit, a thermocouple holder and a sampling unit.

The thermocouple unit 100 is shown in FIG. 1 and comprises a) a first thermocouple 102;
b) a second thermocouple 104;
c) a central part 106 joined to the first and second thermocouples 102, 104. The central part 106 also involves means 108, 110 for connecting the first and second thermocouples 102, 104 to a calculation means; and
d) information transfer means 112 for transferring data relating to the two thermocouples 102, 104.

The thermocouple unit 100 is adapted for recording cooling curves in the manners disclosed in WO 99/25888 and WO 92/06809. The first thermocouple 102 is intended to record cooling curves in the centre of a sample of molten cast iron, whereas the second thermocouple 104 is intended to record cooling curves in a sample of molten cast iron adjacent to the wall of the sample vessel that is used during the analysis. The arrangement of the thermocouples on the central part 106 of the thermocouple unit is therefore adapted to a particular sample that is to be used during the thermal analysis. However, it is easy for the skilled person to design a thermocouple unit in such a way that one thermocouple can be centrally arranged while the other is located near the vessel wall for each given sample vessel. The thermocouples might for instance be welded together in such a way that the second thermocouple 104 ends at a longer distance from the central part 106 than the first thermocouple 102. The central part 106 also has means 108, 110 for connecting the thermocouples 102, 104 to a calculation/computer means, for subsequent presentation and/or evaluation of the results, for instance using the technology disclosed in WO 99/25888 and WO 92/06809.

The first thermocouple 102 is adapted for recording cooling curves in the centre of a molten cast iron sample contained in a sample vessel, and the second thermocouple 104 is adapted for recording cooling curves in the cast iron sample adjacent to the sample vessel wall. Accordingly, the arrangement of the thermocouples 102, 104 on the central unit 106 is dependent on the design of the particular sample vessel that is used. It is easy for the skilled person to adapt the thermocouple arrangement of the thermocouple unit to a given sample vessel design.

The thermocouple unit 100 comprises an information transfer means 112, which preferably is located on the central part. The information transfer means 112 can be a magnetic memory means a printed bar code, or a radio frequency memory tag. The information transfer means contains calibration data relating to the thermocouples 102, 104. Preferably, it also contains serial numbers etc rendering it possible to identify the individual thermocouples of the thermocouple unit, and to identify the calibration factors of these thermocouples to allow automatic correction in the software.

During measurements, it is advantageous to protect the thermocouples against the hot cast iron melt. If the thermocouples are protected, it is possible to reuse them several times. Typically, the thermocouples are inserted into one or two protective tubings. Such protective tubings can either constitute an integral part of the sample vessel, or be put on as a separate fitting when the thermocouple unit is mounted in a thermocouple holder. Such protective tubings are not shown in the figures of the present application.

A thermocouple holder 200 according to the present invention is shown in FIG. 2. It comprises a cylindrical bushing 202 adapted to be fixed to the thermocouples 102, 104 of the thermocouple unit 100. The cylindrical bushing 202 also comprises position indication means 206. The position indication means 206 shown in FIG. 2 is a recess enabling free passage of a light beam (optical detection) when the thermocouples 102, 104 of the thermocouple unit 100 are correctly positioned in the sample vessel. Alternatively, the position indication means can be a permanent magnet (magnetic detection) or a rod (mechanical detection).

As already mentioned the cylindrical bushing 202 is adapted to be fixed to the thermocouples 102, 104 of the thermocouple unit 100 (or optionally to protective tubes surrounding the thermocouples 102, 104) by using suitable means 204, such as screws. Naturally, it is essential that the thermocouples 102, 104 are fixed to the bushing 202 in a position corresponding to the position during the calibrations.

The thermocouple holder 200 also comprises a head part 208 intended to house the central part 106 of the thermocouple holder. The head part has a means 210, such as an opening, for giving access to the information transfer means 112 of the thermocouple unit. Finally, the head part is also equipped with a fastening means 214 for attaching the thermocouple holder to the sampling unit.

The cylindrical bushing 202 and the head part 208 are axially flexibly joined by a suitable means 212, such as a spring.

A sampling unit 300 is shown in FIG. 3. It comprises a housing 302 adapted for containing a thermocouple holder 200 equipped with a thermocouple unit. The unit further involves a means 304 for attaching a sample vessel 306. This means 304 is specifically adapted for the sample vessel type used in a particular assay. Examples of suitable sample vessels are given in WO 99/28726 and WO 96/23206. The means 304 is located on an elongated part 322 intended to enclose the cylindrical bushing 202 of the thermocouple holder 200.

The sampling unit 300 has a means 308 for attaching the head part 208 of the thermocouple holder 200 inside the housing. This means 308 is adapted for being used together with the corresponding fastening means 214 on the head part 208. The fastening mechanism is designed in such a way that it is easy to quickly change the thermocouple holder. It is easy for the skilled person to develop suitable fastening mechanisms. Furthermore, the upper part 318 of the housing is pivotally mounted using one or more hinges 320, in order facilitate exchanging the thermocouple holder 200 inside the hosing 302.

The sampling unit 300 comprises means 314 for reading the information in the information transfer means 112 of the thermocouple unit 100 and to send this identity and/or calibration factor information to a calculating/computer means. The reading means 314 can be a bar code reader a magnetic transducer, or a means for detecting signals from a radio frequency memory tag etc.

The sampling unit 300 further comprises means 310 for moving the cylindrical bushing 202 of the thermocouple holder 200, and thereby the thermocouples 102, 104 of the thermocouple unit 100, between a measuring position and a resting position. It is easy for the skilled person to design suitable means. The means can be controlled by a manual control means 316, or alternatively it can be controlled automatically by the computer means.

The elongated part 322 of the housing 302 also comprises means 312 for detecting whether the position indication means 206 of the cylindrical bushing 202 is in a position corresponding to the measurement position or not. In case the position indication means 206 of the bushing 202 is a recess, the detecting means can be a light source operating together with a light detector. In case the position indication means 206 is correctly positioned, there is a recess in the bushing 202 between the light source and the light detector, and the detector sends a positive signal. In case the position indication means is in another position, less or no light reaches the light detector and no positive signal is sent. The start of the thermal analysis is prevented, or in case it has already begun, it is interrupted.

Alternatively, detection means 312 can be for instance a magnet or a coil when the position is magnetically detected, or for example a switch mechanism when the position is mechanically detected.

The invention claimed is:

1. In combination,
    a thermocouple unit useful in recording cooling curves in connection with thermal analysis of molten cast irons, said thermocouple unit comprising:
        a) a first thermocouple;
        b) a second thermocouple;
        c) a central part joined to said first thermocouple and said second thermocouple, said central part including means for connecting said first and second thermocouples to a calculation device; and
        d) information transfer means to transfer to the calculation device calibration data and/or traceability data relating to said first and second thermocouples, said information transfer means being provided on the central part;
        wherein said first thermocouple is adapted for recording cooling curves in the center of a molten cast iron sample contained in a sample vessel, and said second thermocouple is adapted for recording cooling curves in said cast iron sample adjacent to the sample vessel wall; and
    a thermocouple holder useful in recording cooling curves in connection with thermal analysis of molten cast irons, said thermocouple holder comprising:
        a) a cylindrical bushing adapted to be fixed to the first and second thermocouples of the thermocouple unit, said cylindrical bushing also having a position indicator; and
        b) a head part having a fastener to attach the thermocouple holder to a sampling unit, said head part allowing access to the information transfer means of the thermocouple unit,
        wherein said cylindrical bushing is flexibly coupled to the head part in an axially compliant manner.

2. A combination according to claim 1, wherein the information transfer means includes a bar code, a magnetic memory or a radio frequency memory tag.

3. In combination,
    a thermocouple unit useful in recording cooling curves in connection with thermal analysis of molten cast irons, said thermocouple unit comprising:
        a) a first thermocouple;

b) a second thermocouple;

c) a central pad joined to said first thermocouple and said second thermocouple, said central part including means for connecting said first and second thermocouples to a calculation device; and d) information transfer means to transfer to the calculation device calibration data and/or traceability data relating to said first and second thermocouples said information transfer means being provided on the central part;

wherein said first thermocouple is adapted for recording cooling curves in the center of a molten cast iron sample contained in a sample vessel, and said second thermocouple is adapted for recording cooling curves in said cast iron sample adjacent to the sample vessel wall; and a sampling unit useful in recording cooling curves in connection with thermal analysis of molten cast irons, comprising a housing adapted to contain a thermocouple holder comprising a cylindrical bushing adapted for being fixed to the first and second thermocouples of the thermocouple unit, said cylindrical bushing also having position indicator and a head part having a fastener to attach the thermocouple holder to a sampling unit, said head part allowing access to the information transfer means of the thermocouple unit, wherein said cylindrical bushing is flexibly coupled to the head part in an axially compliant manner, wherein said holder comprises a housing including:

a) means for attaching a sample vessel;

b) means for attaching said thermocouple holder inside the housing;

c) means for moving the cylindrical bushing of the thermocouple holder, and thereby the thermocouples of the thermocouple unit, between a measurement position and a resting position; and d) means for detecting whether the position indicator of said thermocouple holder is in a position corresponding to the measurement position.

4. A combination according to claim 3, wherein the information transfer means includes a bar code, a magnetic memory or a radio frequency memory tag.

5. In combination, a thermocouple unit useful in recording cooling curves in connection with thermal analysis of molten cast irons, said thermocouple unit comprising:

a) a first thermocouple;

b) a second thermocouple;

c) a central part joined to said first thermocouple and said second thermocouple, said central part including means for connecting said first and second thermocouples to a calculation device; and d) an information transfer unit to transfer to the calculation device calibration data and/or traceability data relating to said first and second thermocouples, said information transfer unit being provided on the central part;

wherein said first thermocouple is adapted for recording cooling curves in the center of a molten cast iron sample contained in a sample vessel, and said second thermocouple is adapted for recording cooling curves in said cast iron sample adjacent to the sample vessel wall; and a thermocouple holder useful in recording cooling curves in connection with thermal analysis of molten cast irons, said thermocouple holder comprising:

a) a cylindrical bushing adapted to be fixed to the first and second thermocouples of the thermocouple unit, said cylindrical bushing also having a position indicator; and b) a head part having a fastener to attach the thermocouple holder to a sampling unit, said head part allowing access to the information transfer means of the thermocouple unit, wherein said cylindrical bushing is flexibly coupled to the head part in an axially compliant manner.

6. A combination according to claim 5, wherein the information transfer unit includes a bar code, a magnetic memory or a radio frequency memory tag.

\* \* \* \* \*